(12) United States Patent
Hoshi et al.

(10) Patent No.: US 6,190,683 B1
(45) Date of Patent: *Feb. 20, 2001

(54) BLACKHEAD-REMOVING FACE PACK SHEET

(75) Inventors: Masaru Hoshi; Eiji Suzuki; Hideaki Okabe, all of Kanagawa (JP)

(73) Assignee: Lintec Corporation, Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/919,744

(22) Filed: Aug. 28, 1997

(30) Foreign Application Priority Data

Sep. 3, 1996 (JP) ................................... 8-252502

(51) Int. Cl.[7] .................. A61K 9/70; A01N 25/34; A61L 15/16
(52) U.S. Cl. .................. 424/402; 424/400; 424/401; 424/443; 424/445; 424/446; 424/447; 424/449
(58) Field of Search .................. 424/400, 401, 424/402, 443, 445, 446, 447, 449

(56) References Cited

U.S. PATENT DOCUMENTS

| | | | |
|---|---|---|---|
| 3,598,123 | * 8/1971 | Zaffaroni | 128/268 |
| 4,880,416 | * 11/1989 | Horiuchief et al. | 604/307 |
| 5,338,490 | * 8/1994 | Dietz et al. | 252/500 |
| 5,362,420 | * 11/1994 | Itoh et al. | 252/500 |
| 5,389,376 | * 2/1995 | Duan et al. | 424/448 |

FOREIGN PATENT DOCUMENTS

| | | |
|---|---|---|
| 4-54107 | 2/1992 | (JP) . |
| 4-54108 | 2/1992 | (JP) . |
| 3046929 | 3/1998 | (JP) . |

* cited by examiner

Primary Examiner—José G. Dees
Assistant Examiner—Kathryn E. Shelborne
(74) Attorney, Agent, or Firm—Brinks Hofer Gilson & Lione; G. Peter Nichols (57) ABSTRACT

A blackhead-removing face pack sheet with superior ease of use and blackhead-removing capacity is provided. The blackhead-removing face pack sheet 1 is formed from a laminate which comprises a gas-permeable and flexible base layer 2 and a pack material layer 3 the primary component of which is a copolymer of vinyl acetate and N-vinyl-2-pyrrolidone. The base layer 2 comprises a porous material such as a nonwoven fabric, and part of it is impregnated or embedded with the pack material constituting the pack material layer 3. This gives a high force of adhesion between the base layer 2 and the pack material layer 3.

18 Claims, 1 Drawing Sheet

BLACKHEAD-REMOVING FACE PACK SHEET

BACKGROUND OF THE INVENTION

1. Field of the Invention

This invention relates to a blackhead-removing face pack sheet for removing blackheads formed in pores. This invention also relates to a method for making such a blackhead-removing face pack sheet.

2. Description of the Related Art

Blackheads are formed in the pores of human skin due to secretions such as sebaceous secretions, debris and dust, etc., and these blackheads are undesirable from the point of View of the health and appearance of the complexion. Prior art methods for preventing and eliminating these blackheads include cleaning the face using different face cleaning agents, or the application of liquid face packs contained in tubes.

Although cleaning the face takes a short time and has benefits in preventing blackhead formation, it has been virtually unable to remove blackheads formed in pores.

On the other hand, prior art face packs are coated onto the skin and dried, and then the film that is formed is peeled off to remove blackheads by the force of adhesion to the skin; however the capacity to remove blackheads has been insufficient.

Moreover, with such coating-type face packs it is difficult for the user to coat his/her own skin to an even thickness, and consequently there is variation in the state of dryness, and when the pack film is peeled, the pack material remains on the skin in areas in which it is not dry. Further, there is also the problem in that parts of the film which are thin are liable to break when peeled, and the broken fragments remain on the skin, so that it takes a lot of effort to remove all of the coating film.

In order to eliminate such drawbacks, it is necessary to coat the pack on thick, and allow a longer time for it to dry; however, besides being inconvenient and detracting from practical usefulness, this also means that a lot of the pack is consumed, which is economically disadvantageous.

SUMMARY OF THE INVENTION

An object of the present invention is to provide a blackhead-removing face pack sheet which is easy to use and can remove blackheads efficiently in a short time.

In order to achieve the object, the present invention is directed to a blackhead-removing face pack sheet including a laminate, the laminate comprising:

a gas-permeable and flexible base layer, and a pack material layer disposed on the base layer, the pack material layer containing a copolymer of vinyl acetate and N-vinyl-2-pyrrolidone as its primary ingredient.

The blackhead-removing face pack sheet according to the present invention can give efficient removal of blackheads in a short time. Further, the face pack sheet does not leave residues of the pack material on the skin on peeling. In this way, it is possible, by using a simple and convenient procedure, to clean the pores and maintain a good complexion.

In the present Invention, It is preferred that the copolymer has an average molecular weight of 10,000–500,000.

Further, it is also preferred that the copolymer has been copolymerized at a ratio of vinyl acetate to N-vinyl-2-pyrrolidone of 5:95 to 95:5.

Furthermore, it is also preferred that the pack material layer has a content of the copolymer of 20–90% by weight.

In this case, it is preferred that the pack material layer contains vinyl acetate homopolymer and/or N-vinyl-2-pyrrolidone homopolymer.

Moreover, in the present invention, it is preferred that the base layer comprises a porous material.

In this case, it is preferred that the substance constituting the pack material layer is partly impregnated or embedded in the base layer. Further, it is also preferred that the surface of the base layer having the pack material layer disposed thereon has been subjected to a hydrophilization treatment.

Moreover, in the present invention, it is preferred that the pack material layer has been formed by coating or transfer.

Further, the pack material layer may contain a plasticizer which exhibits a plasticizing action on the copolymer, or a filler.

Furthermore, in the present invention, it is preferred that the pack material layer contains a medium comprising a lower alcohol and/or water.

Another aspect of the present invention is directed to a method for making a blackhead-removing face pack sheet. The method comprises the step of providing a gas-permeable and flexible base layer; and coating a pack material containing a copolymer of vinyl acetate and N-vinyl-2-pyrrolidone as its primary ingredient on one side of the base layer to form a pack material layer.

In this method, it is preferred that the pack material layer contains vinyl acetate homopolymer and/or N-vinyl-2-pyrrolidone homopolymer.

The other aspect of the present invention is directed to a method for making a blackhead-removing face pack sheet. This method comprises the step of providing a gas-permeable and flexible base layer; and joining a pack material layer formed of a pack material containing a copolymer of vinyl acetate and N-vinyl-2-pyrrolidone as its primary ingredient onto one side of the base layer by transferring the pack material layer onto the base layer.

In this method, it is preferred that the pack material layer contains vinyl acetate homopolymer and/or N-vinyl-2-pyrrolidone homopolymer.

The present invention is also directed to a method for making a blackhead-removing face pack sheet including a laminate which comprises a gas-permeable and flexible base layer and a pack material layer formed of a pack material containing a copolymer of vinyl acetate and N-vinyl-2-pyrrolidone as its primary ingredient. This method comprises the steps of forming the pack material layer on a transfer medium; moistening the pack material layer and/or the base layer with water; and transferring the pack material layer from the transfer medium onto one surface of the base layer to join the pack material layer and the base layer, and pressing both the pack material layer and the base layer together.

The present invention is also directed a method for making a blackhead-removing face pack sheet including a laminate which comprises a gas-permeable and flexible base layer and a pack material layer formed of a pack material containing a copolymer of vinyl acetate and N-vinyl-2-pyrrolidone as its primary ingredient. The method comprises the steps of forming the pack material layer on a transfer medium; moistening the pack material layer and/or the base layer with water; and transferring the pack material layer from the transfer medium onto one surface of the base layer to join the pack material layer and the base layer, and then pressing both the pack material layer and the base layer so as to partly impregnate or embed the substance constituting the pack material layer in a part of the base layer.

In this case, it is preferred that the pack material layer contains vinyl acetate homopolymer and/or N-vinyl-2-pyrrolidone homopolymer.

Other objects, constructions and effects of the present invention will be apparent to a person having ordinary skill in the art when the following description of the preferred embodiments are considered taken in conjunction with the accompanying drawings.

DETAILED DESCRIPTION OF THE INVENTION

The blackhead-removing face pack sheet of the present invention and methods for making it are described in detail below.

Figure 1:
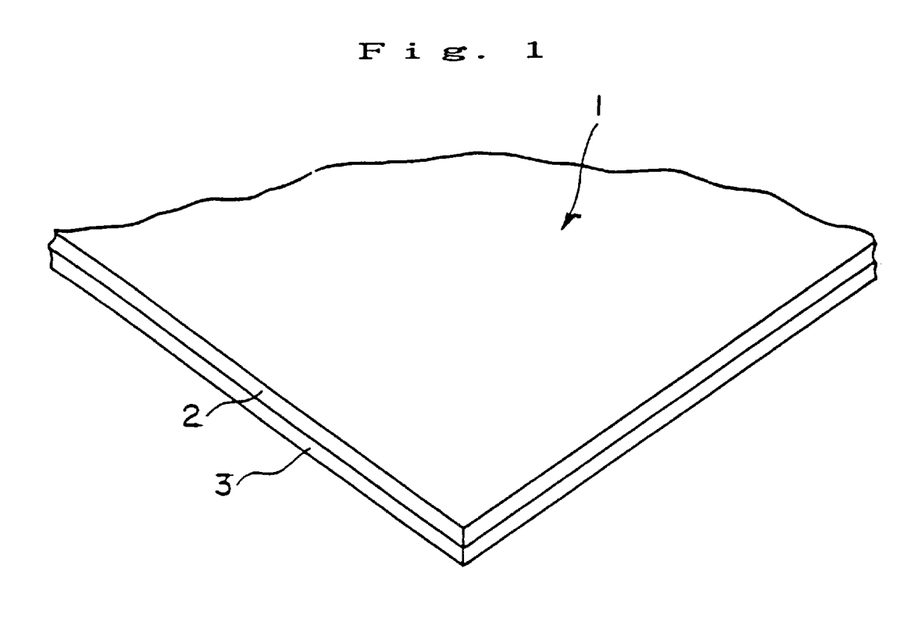
FIG. 1 is a perspective View of an embodiment of the blackhead-removing face pack sheet of the present invention.

FIG. 1 is a perspective view showing an embodiment of the blackhead-removing face pack sheet of the present invention. As the drawing shows, the blackhead-removing face pack sheet 1 of the present invention is formed by laminating a base layer 2 and a pack material layer 3. The constitution of each of the layers will be explained below.

The base layer 2 has a predetermined gas permeability and flexibility (softness). Such base layer 2 may comprise a porous material. Exemplary porous materials include non-fibrous and fibrous porous materials.

Examples of non-fibrous porous material include membrane filters, foams (polypropylene foam, polyethylene foam, polyurethane foam, etc.), various types of porous films and meshes, etc.

Examples of fibrous porous materials include weaves, nonwoven fabrics, papers and agglomerates of short fibers, etc. Weaves here include knits and weaves such as woven fabrics and related products. The weave structure can be any structure suitable for practical use, including plain weave, twill weave and crepe weave, etc. Similarly, there are no specific restrictions as to knitted structure, which can be weft knit (plain knit), warp knit (tricot knit), purl knit, flattened or stockinette knit, etc., for example. When nonwoven fabric is used there is no specific restriction as to the packing density of the fibers (bulk density). As paper, ordinary paper (western paper or Japanese paper) or laminates thereof, or a variety of synthetic paper, can be used.

Examples of fiber constituents of such fibrous porous materials include natural fibers such as cellulose fibers, cotton, linter, kapok, flax, hemp, ramie, silk and wool, etc., chemical fibers such as nylon (polyamide), tetron, rayon, cupra, acetate, vinylon, acrylic, poly(ethylene terephthalate) (polyester) and polypropylene, etc., and combinations of two or more of these natural and chemical fibers (mixed yarns, etc.). The thickness of these fibers will depend on the type of fiber, but the order of 0.1–5.0 denier is usually preferred.

Such base layers 2 are preferably gas permeable in themselves. The reason is to allow the medium (moisture, alcohol, etc.) in the pack material layer 3 to pass through the base layer 2 and evaporate when the pack material layer 3, described below, is stuck to the skin, so that the pack material layer 3 can dry evenly.

The base layer 2 is preferably flexible. The reason is to enable the blackhead-removing face pack sheet 1 to follow curved skin surfaces when it is stuck to such surfaces such as the curves of the face around the nose for example.

The primary component of the pack material constituting the pack material layer 3 is a copolymer of vinyl acetate and N-vinyl-2-pyrrolidone.

Compared with the homopolymer of vinyl acetate or the homopolymer of N-vinyl-2-pyrrolidone, copolymers of vinyl acetate and N-vinyl-2-pyrrolidone (also referred to below as "copolymers") have higher adhesion strength when stuck to skin, and a greater capacity for removing blackheads, and layers of such copolymers are also less prone to tear and less prone to leave residues on the skin when they are peeled.

The copolymerization ratio in the vinyl acetate/N-vinyl-2-pyrrolidone copolymer can be selected at will, but the range 5:95 to 95:5 is preferred, the range 15:85 to 85:15 is more preferred, and the range 30:70 to 70:30 is even more preferred. Within such ranges particularly good blackhead removing performance is manifested.

The copolymer of vinyl acetate and N-vinyl-2-pyrrolidone can be any form of copolymer, such as a random copolymer, block copolymer or graft copolymer, etc.

There are no specific restrictions as to the average molecular weight of the copolymer of vinyl acetate and N-vinyl-2-pyrrolidone; however, it is preferably of the order of 10,000–500,000, and more preferably of the order of 20,000–200,000. If the average molecular weight is too low, the membrane strength of the pack material layer 3 is low and residues of the pack material layer are prone to be left on the skin; and if the average molecular weight is too high, solubility in water becomes low and the strength of adhesion to the skin may be insufficient.

The content of copolymer of vinyl acetate and N-vinyl-2-pyrrolidone in the pack material layer 3 is preferably of the order of 20–90% by weight, and more preferably of the order of 40–80% by weight. If this content is too low, there is little benefit in terms of raised blackhead-removing capacity, and if it is excessive, the pack material layer 3 becomes hard, which leads to cracking and difficulties with handling.

The pack material constituting the pack material layer 3 may also include either vinyl acetate homopolymer or N-vinyl-2-pyrrolidone homopolymer, or both, in addition to the aforementioned copolymer. The addition of vinyl acetate homopolymer contributes to raising the membrane strength of the pack material layer 3, and effectively prevents portions of the pack material layer 3 (and particularly the edges) from remaining on the skin when the blackhead-removing face pack sheet 1 is peeled from the skin. The addition of N-vinyl-2-pyrrolidone homopolymer contributes to raising the solubility of the pack material in water, and can raise the closeness of adhesion of the face pack sheet 1 to the skin.

The total content of such vinyl acetate homopolymer and N-vinyl-2-pyrrolidone homopolymer is preferably of the order of 0.01–40% by weight, and more preferably of the order of 0.1–30% by weight.

The pack material constituting the pack material layer 3 may optionally contain various types of additives mentioned below.

An exemplary additive is a plasticizer which has the action of plasticizing said copolymer. Preferable plasticizers are compounds and oils (hereinafter referred to as "oils") as mentioned below.

Examples of plasticizers which can be used include: polyhydric alcohol such as ethylene glycol, diethylene glycol, triethylene glycol and higher polyethylene glycols; propylene glycol and polypropylene glycols; butanediols such as 1,3-butanediol and 1,4-butanediol, etc.; glycerin, diglycerin, triglycerin and higher polyglycerins, etc.; hydrocarbons such as liquid paraffin, squalane, vaseline and solid paraffin, etc.; natural oils such as jojoba oil, castor oil, olive oil, egg yolk oil and palm oil, etc.; silicone oils such as poly(dimethylsiloxane), etc.; higher fatty acids such as oleic acid and isostearic acid, etc.; higher alcohols such as lauryl alcohol, etc.; esters such as isopropyl myristate, etc.; nonionic surfactants such as glycerin fatty acid esters, sorbitan fatty acid esters, polyoxyethylene sorbitan fatty acid esters, polyoxyethylene castor oil, polyoxyethylene hardened castor oil, and polyoxyethylene alkyl ether, etc.; anionic surfactants such as N-acylamino acid salts etc.; cationic surfactants such as aliphatic quaternary ammonium salts, etc.; and amphoteric surfactants such as betaines, etc.

The content of these plasticizers in the pack material layer 3 is preferably of the order of 0.01–30% by weight, and more preferably of the order of 1–20% by weight. If the plasticizer content is too small then, depending on the average molecular weight and content of said copolymer, the pack material layer 3 may become hardened, making it prone to cracking and difficult to handle; and if the content of plasticizer is excessive then, depending on the average molecular weight and content of said copolymer, the pack material layer 3 may become softened, so that the force of adhesion to the skin is low and removal of blackheads becomes insufficient.

Other additives which can be added to the pack material include fillers. Pigments can be cited as typical fillers. Examples of pigments include inorganic pigments such as talc, sericite, calcium carbonate, kaolin, anhydrous silicic acid, hydrated silicic acid, titanium oxide and mica titanium, etc., organic pigments such as powdered polyamides, polyethylene, cellulose and poly(methyl methacrylate), etc. (especially spherical powders), and such fillers rendered water-repellant by treatment with metal soaps, esters, silicone, etc.

The content of such fillers (especially pigments) is preferably not more than 60% by weight, and more preferably of the order of 1–40% by weight. When the content of fillers is excessive, blackhead removing capacity is weakened.

In addition, polymers such as homopolymers or copolymers of common monomers such as vinyl alcohol, vinyl alkyl ethers, styrene, alkyl-substituted styrenes, (meth) acrylic acid, (meth)acrylates, vinyl butyral, vinyl formal, acrylamides, N-alkylacrylamides, N-vinylacetamide, allylamine, ethyleneimine, acrylonitrile, a-amino acids, styrenesulphonic acid and salts thereof, etc., and alginic acid, alginate, starch, cellulose and cellulose derivatives (HEC and CMC), etc., can be added to the pack material. The content of these substances is preferably of the order of 0.01–20% by weight, and more preferably of the order of 0.1–10% by weight.

Other additives include preservatives, bacteriocides, antioxidants, flame retardants and humectants, etc., for example; these can be added within ranges within which they do not diminish the blackhead-removing capacity of the pack material.

The pack material layer 3 can also include unvolatilized content of medium (or dispersion medium) added in the process of preparing the pack material. Such medium (and dispersion medium) include water (inorganic medium), and lower alcohols such as ethanol and isopropanol, etc. (organic medium); one or more of these can be used.

The quantity of medium in the pack material layer 3 is preferably not more than 30% by weight, and more preferably not more than 20% by weight. In particular, the content of such medium (especially lower alcohols) can be extremely low.

The base layer 2 and pack material layer 3 can be joined (bonded) with a certain force of adhesion.

Figure 2:
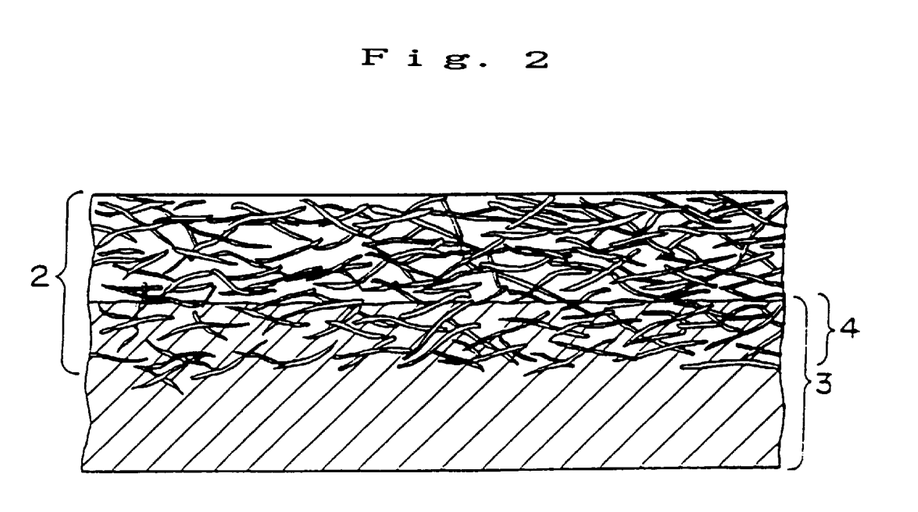
FIG. 2 is an exploded cross-sectional view schematically showing the laminate constitution of the blackhead-removing face pack sheet of the present invention.

The force of adhesion between the base layer 2 and the pack material layer 3 can be obtained, for example, by bonding the base layer 2 and the pack material layer 3 with an adhesive; however, in the present invention the pack material, which is the substance constituting the pack material layer 3, is preferably impregnated or embedded in a part of the base layer 2 (partially in the direction of thickness), as shown schematically in FIG. 2. This enables a high force of adhesion to be obtained between the base layer 2 and the pack material layer 3 with a simple layer structure (and simple manufacturing process), and has the benefit of preventing part of said pack material layer remaining on the skin.

With such a constitution, the interface between the base layer 2 and the pack material layer 3 is not necessarily clearly defined, and in the vicinity of the interface between the two layers 2 and 3, the two layers 2 and 3 overlap (see FIG. 2). In this case, the thickness of the overlap 4 of the two layers 2 and 3, i.e. the thickness of the portion in which the pack material layer 3 is embedded in the base layer 2, is preferably of the order of 1–80%, and more preferably of the order of 5–50%, of the total thickness of the base layer 2.

FIG. 2 shows the base layer 2 as a fibrous porous material; however, when the base layer 2 is of a non-fibrous porous material, the pack material can be impregnated (embedded) in the recess or pores in the surface of the base layer 2, to obtain similar benefits in terms of raised force of adhesion to those described previously.

There are no restrictions as to methods for forming such a pack material layer 3; however, for reasons of ease of formation, stability and productivity, etc., it is preferably formed by direct coating or transfer.

The pack material layer 3 can be formed easily and accurately by direct coating or transfer; and there are the advantages that it is easy to obtain an overlapping structure of layers 2 and 3 shown in FIG. 2, and it is easy to control the constitution of the layers. Direct coating and transfer methods will be described later in further detail.

The thickness of the base layer 2 is adequately selected in accordance with the material of the base layer. The base layer, however, preferably has a thickness of the order of 0.05–1 mm, and more preferably of the order of 0.1–0.5 mm.

There are no specific restrictions as to the thickness on the pack material layer; however, it is also preferably of the order of 0.5–1 mm, and more preferably of the order of 0.1–0.3 mm.

Next, methods for making a blackhead-removing face pack sheet of the present invention will be explained. Blackhead-removing face pack sheets of the present invention can be made for example by the method below.

1. Coating

A pack coating solution is first prepared for forming the pack material layer 3. The pack coating solution is prepared by mixing the predetermined quantities of the copolymer of vinyl acetate and N-vinyl-2 pyrrolidone and the optionally added homopolymers, the additives and the inorganic and/or organic medium, and stirring the mixture. The viscosity of the pack coating solution can be, for example, of the order of 100–5000 cps.

This pack coating solution is then coated onto one side of the base layer 2, and dried. By this means a laminate of the base layer 2 and the pack material layer 3 is obtained. The method of coating can be coating using a roller, air knife, knife, conma, gravure, mayer bar, or a fountain die method, or spray coating, brush painting or dipping, etc., for example.

When the base layer 2 comprises a porous material as described previously, part of the pack coating solution permeates into the porous material during the coating, constituting partial impregnation or embedding of the pack material into the base layer 2, as shown in FIG. 2.

The base layer 2 can be subjected to prior treatment to make it hydrophilic or hydrophobic (water repellant), etc., as appropriate for the constituent material and the surface thereof. For example, the surface of the base layer 2 which is coated with the pack coating solution (pack coating surface) can be subjected to treatment to render it hydrophilic, or the surface of the base layer 2 opposite the pack coating surface can be treated to render it hydrophobic (water-repellant), or both can be performed. The conditions such as depth of permeation of the pack coating solution into the porous material (base layer 2) can be appropriately controlled by performing such treatments. Similarly, a laminate of any combination of two or more of porous sheet material subjected to hydrophilic treatment, porous sheet material subjected to hydrophobic (water-repellant) treatment, and porous sheet material not subjected to these treatments, can be used; such cases also give benefits similar to those above.

Exemplary hydrophilic treatments are those utilizing a surfactant and plasma treatment; and exemplary hydrophobic (water repellant) treatments are those utilizing silicone compounds or fluorine compounds.

2. Transfer method A

A pack coating solution is prepared as described previously, and this pack coating solution is coated onto the surface of a transfer (intermediate) medium such as a film, etc., and dried to form the pack material layer 3.

Then, this pack material layer 3 is superimposed on the base layer 2, and transferred to the surface of the base layer 2 by removing the transfer medium. This gives a laminate of the base layer 2 and pack material layer 3. It is to be noted that, in transferring the pack material layer 3 onto the base layer 2, an intervening layer such as an adhesive layer may be disposed on the base layer 2.

The same applies as before to hydrophilic treatment and hydrophobic (water-repellant) treatment of the base layer 2.

3. Transfer method B

The pack material layer 3 is formed on a transfer medium as in said transfer method A.

Then, the moisture content of the pack material layer 3 and/or the base layer 2 is increased by moistening the pack material layer 3 and/or the base layer 2.

The pack material layer 3 and the base layer 2 are then laminated and pressed by rollers, etc. By such treatment, the pack material is softened, and the softened pack material becomes embedded in the base layer 2 to bring about the state shown in FIG. 2. The strength of adhesion between the base layer 2 and the pack material layer 3 is thereby increased.

For the moistening treatment, a generally used method, including steam damping, ultrasonic moisturizing, spraying, rotor tumbling, dipping, and coating methods such as brush coating, roller coating or gravure coating, etc., can be used.

The same applies to hydrophilic treatment and hydrophobic (water-repellant) treatment of the base layer 2.

With the methods for making blackhead-removing face pack sheet as described above, it is possible to easily make the blackhead-removing face pack sheets having the outstanding benefits as described above. More particularly, the thicknesses and degree of overlap, etc., can easily be controlled, and the pack material layer can also be formed to an even thickness. Productivity is also high and the methods are suitable for mass production.

The present invention is hereinafter explained in further detail by referring to Examples of the invention and Comparative Examples.

EXAMPLES

Examples 1–7

Pack coating solutions were prepared with the compositions shown in the attached Table 1.

In the ethanol solution of the copolymer of vinyl acetate and N-vinyl-2-pyrrolidone were added the solution of vinyl acetate homopolymer and/or N-vinyl-2-pyrrolidone homopolymer, and the filler, and then they were stirred.

The plasticizer/oil was then dissolved or dispersed in water, and the solution or dispersion was added to the copolymer solution. The solution was thoroughly stirred to produce the pack coating solution. The viscosity of the resulting pack coating solution was 500–1500 cps.

Meanwhile, a nonwoven polyester fiber fabric (0.4 mm thick) was prepared for the base layer.

The pack coating solution was coated on the surface of transfer film, and dried to form the pack material layer with a dry film thickness of 0.15 mm. The pack material layer was then softened by moistening treatment using steam damping, after which the pack material layer was laminated with the base layer. The laminate was then pressed with rollers so that the softened pack material would partly permeate into the base layer and became embedded in it. The thickness of the overlap between the base layer and pack material layer was of the order of 20% of the thickness of the base layer.

The blackhead-removing face pack sheets of the present invention were prepared as described above.

Examples 8–14

Pack coating solutions with the compositions shown in the attached Table 2 were prepared by repeating the above-described procedure. The viscosity of the coating solutions was 500–1500 cps.

Meanwhile, porous polypropylene film (thickness 0.05 mm) was prepared for the base layer. The surface of this base layer that was to be joined with the pack material layer was sprayed with a surfactant to hydrophilize the surface to thereby improve the adhesion of the pack coating. The film was then dried.

The coating solution was then coated onto one side of the base layer (the side subjected to hydrophilic treatment), and dried to form the pack material layer of a dry thickness of 0.15 mm.

Blackhead-removing face pack sheets of the present invention were thus prepared.

Examples 15–17

Pack coating solutions with the compositions shown in the attached Table 3 were prepared by repeating the above-described procedure. Blackhead-removing face pack sheets of the present invention were made by repeating the procedures of Examples 8–14 except that that a cotton weaven fabric (thickness 0.5 mm) was used as the base layer.

The thickness of the overlap between the base layer and the pack material layer was about 20% of the thickness of the base layer.

Comparative Examples 1 and 2

Pack coating solutions with the compositions shown in the attached Table 3 were prepared by repeating the above-described procedure. The pack coating solution was coated on the base layer which is the same as the one used in Examples 1 to 7 to form the pack material layer. The blackhead-removing face pack sheets were thereby prepared.

Comparative Examples 3 and 4

Pack coating solutions with the compositions shown in the attached Table 3 were prepared by repeating the above-described procedure. The pack coating solution was coated on one side of the base layer comprising a porous polypropylene film (thickness 0.05 mm) and dried to form the pack material layer having a dry thickness of 0.15 mm. The blackhead-removing face pack sheets were thereby prepared.

Experiment 1

The blackhead-removing face pack sheets (n=3) of the above-described Examples 1–17 and Comparative Examples 1–4 were stuck to the nose and the surrounding skin of human subjects after washing the face, and left for 15 minutes at ordinary temperature and ordinary humidity (30 minutes in the case of Comparative Example 3 and 4). During this time, the majority of the medium in the pack material evaporated through the base layer, and the pack material layer became sufficiently dried. The blackhead-removing face pack sheets were then peeled from the skin. After peeling, the pack material layer was observed to evaluate the degree of blackhead removal in terms of the number of blackheads per unit area on the peeled packed material. The results are shown in the attached Table 4.

Experiment 2

The blackhead-removing face pack sheets (n=3) were stuck to the nose and the surrounding skin of human subjects after washing the face, and left for 15 minutes at ordinary temperature and ordinary humidity (30 minutes in the case of Comparative Example 3 and 4). The sheet was then peeled from the skin at a constant speed from one corner, and the degree to which the pack material remained on the skin (area remaining on the skin) was evaluated.

The results are shown in the attached Table 5.

Experimental Results and Discussion

As shown in Tables 4 and 5, the blackhead-removing face pack sheets of Examples 1–17 all manifested an excellent blackhead-removing capacity with a short time of adhesion; and they were very easy to use, leaving hardly any residues of the pack material on the skin after peeling from the skin.

By contrast, the blackhead-removing face pack sheets of Comparative Examples 1–4 had low blackhead-removing capacity; and Comparative Examples 3 and 4 in particular were difficult to handle, with a large proportion of the pack material remaining on the skin after peeling and taking time and trouble to remove.

BENEFITS OF THE INVENTION

As described above, the present invention provides blackhead-removing face pack sheets which give efficient removal of blackheads in a short time, and which do not leave residues of the pack material on the skin on peeling. In this way, it is possible, by using a simple and convenient procedure, to clean the pores and maintain a good complexion.

In addition, the methods of the present invention for making a blackhead-removing face pack sheet makes it possible to make easily a blackhead-removing face pack sheet having said benefits.

Finally, it is to be noted that the present invention is not limited to the embodiments and the examples described above and any changes and modifications can be made without departing from the scope and spirit of the present invention which is defined by the following claims.

TABLE 1

Composition of the pack coating solution unit: % by weight

| | Example 1 | Example 2 | Example 3 | Example 4 | Example 5 | Example 6 | Example 7 |
|---|---|---|---|---|---|---|---|
| P (VAc - co - VP) [*1] Copolymerization ratio = 7:3 Average molecular weight = about 40.000 | — | — | — | — | 39 (79.6) | — | — |
| P (VAc -co - VP) [*1] Copolymerization ratio = 5:5 Average molecular weight = about 60.000 | — | — | 39 (79.6) | — | — | — | 39 (78.0) |
| P (VAc -co - VP) [*1] Copolymerization ratio = 4:6 Average molecular weight = about 50.000 | 30 (62.2) | 33 (66.3) | — | — | — | 33 (66.3) | — |
| P (VAc - co - VP) [*1] Copolymerization ratio = 3:7 Average molecular weight = about 50,000 | — | — | — | 38 (73.1) | — | — | — |
| PVAc [*2] | 0.5 (1.04) | 4 (8.05) | — | — | — | 4 (8.05) | 4 (8.00) |
| PVP [*3] | — | — | 3 (6.11) | 3 (5.75) | 3 (6.11) | — | — |
| Polyoxyethylene hardened castor oil | 1 (2.06) | 1 (2.01) | 0.5 (1.02) | 0.5 (0.96) | 0.5 (1.02) | — | — |
| Polyoxyethylene nonylphenyl ether | — | — | — | — | — | 1 (2.01) | 0.5 (1.00) |
| Castor oil | 2 (4.15) | 1 (2.01) | — | — | 0.5 (1.02) | 1 (2.01) | — |
| Squalane | 2 (4.15) | 1 (2.01) | 0.5 (1.02) | 0.5 (0.96) | — | 1 (2.01) | 0.5 (1.00) |
| Glycerin | 2 (4.15) | 1 (2.01) | 1 (2.04) | 1 (1.91) | 1 (2.04) | — | — |
| 1,3-butanediol | — | — | — | — | — | 1 (2.01) | 1 (2.00) |

TABLE 1-continued

Composition of the pack coating solution unit: % by weight

| | Example 1 | Example 2 | Example 3 | Example 4 | Example 5 | Example 6 | Example 7 |
|---|---|---|---|---|---|---|---|
| Silica | 10 (20.7) | 8 (16.1) | 4 (8.16) | 8 (15.4) | 4 (8.16) | 8 (16.1) | 4 (8.00) |
| Titanium oxide | 0.5 (1.04) | 0.5 (1.00) | 1 (2.04) | 1 (1.91) | 1 (2.04) | 0.5 (1.00) | 1 (2.00) |
| Ethanol | 30 (0.01) | 33.5 (0.01) | 51 (0.01) | 48 (0.01) | 51 (0.01) | 33.5 (0.01) | 50 (0.01) |
| Water | 22 (0.50) | 17 (0.50) | — | — | — | 17 (0.50) | — |

The numbers given in parentheses designates the content of the component in the pack material
[*1] Copolymer of vinyl acetate and N-vinyl-2-pyrrolidone
[*2] Polyvinyl acetate
[*3] Poly (N-vinyl-2-pyrrolidone)

TABLE 2

Composition of the pack coating solution unit: % by weight

| | Example 8 | Example 9 | Example 10 | Example 11 | Example 12 | Example 13 | Example 14 |
|---|---|---|---|---|---|---|---|
| P (VAc - co - VP) [*1] Copolymerization ratio = 7:3 Average molecular weight = about 40,000 | 35 (60.0) | — | — | — | — | — | 33 (56.6) |
| P (VAc - co - VP) [*1] Copolymerization ratio = 5:5 Average molecular weight = about 60,000 | — | 35 (60.0) | — | — | — | 33 (66.3) | — |
| P (VAc - co - VP) [*1] Copolymerization ratio = 4:6 Average molecular weight = about 50,000 | — | — | 35 (60.0) | — | 33 (66.3) | — | — |
| P (VAc -co - VP) [*1] Copolymerization ratio = 3:7 Average molecular weight = about 50,000 | — | — | — | 35 (60.0) | — | — | — |
| PVAc [*2] | 2 (3.46) | 2 (3.46) | 2 (3.46) | 2 (3.46) | 4 (8.05) | — | 2 (3.44) |
| PVP [*3] | — | — | — | — | — | 4 (8.05) | 2 (3.44) |
| Polyoxyethylene hardened castor oil | 0.5 (0.86) | 0.5 (0.86) | 0.5 (0.86) | 0.5 (0.86) | 1 (2.01) | — | 0.5 (0.86) |
| Polyoxyethylene nonylphenyl ether | — | — | — | — | — | 1 (2.01) | — |
| Castor oil | — | — | — | — | 1 (2.01) | 1 (2.01) | — |
| Squalane | 1 (1.73) | 1 (1.73) | 1 (1.73) | 1 (1.73) | 1 (2.01) | 1 (2.01) | 1 (1.72) |
| Glycerin | 3 (5.16) | 3 (5.16) | 3 (5.16) | 3 (5.16) | 1 (2.01) | — | 3 (5.16) |
| 1,3-butanediol | — | — | — | — | — | 1 (2.01) | — |
| Silica | 15 (25.7) | 15 (25.7) | 15 (25.7) | 15 (25.7) | 8 (16.1) | 8 (16.1) | 15 (25.7) |
| Titanium oxide | 1.5 (2.58) | 1.5 (2.58) | 1.5 (2.58) | 1.5 (2.58) | 0.5 (1.00) | 0.5 (1.00) | 1.5 (2.57) |
| Ethanol | 35 (0.01) | 35 (0.01) | 35 (0.01) | 35 (0.01) | 33.5 (0.01) | 33.5 (0.01) | 35 (0.01) |
| Water | 7 (0.50) | 7 (0.50) | 7 (0.50) | 7 (0.50) | 17 (0.50) | 17 (0.50) | 7 (0.50) |

The numbers given in parentheses designates the content of the component in the pack material
[*1] Copolymer of vinyl acetate and N-vinyl-2-pyrrolidone
[*2] Polyvinyl acetate
[*3] Poly(N-vinyl-2-pyrrolidone)

TABLE 3

Composition of the pack coating solution unit: % by weight

| | Example 15 | Example 16 | Example 17 | Comp. Ex. 1 | Comp. Ex. 2 | Comp. Ex. 3 | Comp. Ex. 4 |
|---|---|---|---|---|---|---|---|
| P (VAc - co - VP) [*1] Copolymerization ratio = 7:3 Average molecular weight = about 40,000 | — | — | — | — | — | — | — |
| P (VAc - co - VP) [*1] Copolymerization ratio = 5:5 Average molecular weight = about 60,000 | — | 35 (60.0) | — | — | — | — | — |
| P (VAc - co - VP) | 33 (66.3) | — | — | — | — | — | — |

TABLE 3-continued

Composition of the pack coating solution unit: % by weight

|  | Example 15 | Example 16 | Example 17 | Comp. Ex. 1 | Comp. Ex. 2 | Comp. Ex. 3 | Comp. Ex. 4 |
|---|---|---|---|---|---|---|---|
| Copolymerization ratio = 4:6 Average molecular weight = about 50.000 |  |  |  |  |  |  |  |
| P (VAc - co - VP) [*1] Copolymerization ratio = 3:7 Average molecular weight = about 50.000 | — | — | 38 (73.1) | — | — | — | — |
| PVA [*2] | 4 (8.05) | 2 (3.46) | — | 30.5 (63.2) | — | 30.5 (63.2) | — |
| PVP [*3] | — | — | 3 (5.75) | — | 37 (74.4) | — | 37 (74.4) |
| Polyoxyethylene hardened castor oil | 1 (2.01) | 0.5 (0.86) | 0.5 (0.96) | 1 (2.07) | 1 (2.00) | 1 (2.07) | 1 (2.00) |
| Polyoxyethylene nonylphenyl ether | — | — | — | — | — | — | — |
| Castor oil | 1 (2.01) | — | — | 2 (4.16) | 1 (2.00) | 2 (4.16) | 1 (2.00) |
| Squalane | 1 (2.01) | 1 (1.73) | 0.5 (0.96) | 2 (4.16) | 1 (2.00) | 2 (4.16) | 1 (2.00) |
| Glycerin | 1 (2.01) | 3 (5.16) | 1 (1.91) | 2 (4.16) | 1 (2.00) | 2 (4.16) | 1 (2.00) |
| 1,3-butanediol |  |  |  |  |  |  |  |
| Silica | 8 (16.1) | 15 (25.7) | 8 (15.4) | 10 (20.7) | 8 (16.1) | 10 (20.7) | 8 (16.1) |
| Titanium oxide | 0.5 (1.00) | 1.5 (2.58) | 1 (1.91) | 0.5 (1.04) | 0.5 (1.00) | 0.5 (1.04) | 0.5 (1.00) |
| Ethanol | 33.5 (0.01) | 35 (0.01) | 48 (0.01) | 30 (0.01) | 33.5 (0.01) | 30 (0.01) | 33.5 (0.01) |
| Water | 17 (0.50) | 7 (0.50) | — | 22 (0.50) | 17 (0.50) | 22 (0.50) | 17 (0.05) |

The numhers given in parentheses designates the content of the component in the pack material
[*1] Copolymer of vinyl acetate and N-vinyl-2-pyrrolidone
[*2] Polyvinyl acetate
[*3] Poly (N-vinyl-2-pyrrolidone)

TABLE 4

Results of blackhead removal test

|  | Example 1 | Example 2 | Example 3 | Example 4 | Example 5 | Example 6 | Example 7 |
|---|---|---|---|---|---|---|---|
| Capacity of blackhead removal [*1] | ○ | ◎ | ○ | ○ | ○ | ◎ | ○ |

|  | Example 8 | Example 9 | Example 10 | Example 11 | Example 12 | Example 13 | Example 14 |
|---|---|---|---|---|---|---|---|
| Capacity of blackhead removal [*1] | ○ | ◎ | ◎ | ○ | ◎ | ○ | ○ |

|  | Example 15 | Example 16 | Example 17 | Comp. Ex. 1 | Comp. Ex. 2 | Comp. Ex. 3 | Comp. Ex. 4 |
|---|---|---|---|---|---|---|---|
| Capacity of blackhead removal [*1] | ◎ | ◎ | ○ | X | X | X | X |

[*1] Number of blackheads on the peeled packing material
X: 0 to 5 per cm$^2$.
Δ: 6 to 10 per cm$^2$.
○: 11 to 15 per cm$^2$, and
◎: 16 or more per cm$^2$.

TABLE 5

Results of packing material residue test n = 3

|  | Example 1 | Example 2 | Example 3 | Example 4 | Example 5 | Example 6 | Example 7 |
|---|---|---|---|---|---|---|---|
| Percentage of the remaining packing material [*1] | ○ | ◎ | ○ | ○ | ◎ | ◎ | ◎ |

|  | Example 8 | Example 9 | Example 10 | Example 11 | Example 12 | Example 13 | Example 14 |
|---|---|---|---|---|---|---|---|
| Percentage of the remaining packing material [*1] | ○ | ◎ | ○ | ○ | ○ | ◎ | ○ |

TABLE 5-continued

Results of packing material residue test

| | Example 15 | Example 16 | Example 17 | Comp. Ex. 1 | Comp. Ex. 2 | Comp. Ex. 3 | Comp. Ex. 4 (n = 3) |
|---|---|---|---|---|---|---|---|
| Percentage of the remaining packing material [*1] | ⊙ | ⊙ | ○ | Δ | X | X | X |

[*1](Area of the packing material remaining on the skin/Area onto which the sheet had been adhererd) × 100 (%)
X: more than 10%,
Δ: 6 to 10%,
○: more than 3 to 6%, and
⊙: not more than 3%.

What is claimed is:

1. A blackhead-removing face pack sheet including a laminate, which comprises:
    a gas-permeable and flexible base layer; and
    a pack material layer formed of a pack material that is soluble in water and contains a copolymer of vinyl acetate and N-vinyl-2-pyrrolidone having an average molecular weight of 10,000–500,000 as its primary ingredient, said pack material layer being laminated onto the base layer so that the substance constituting said pack material layer is partly impregnated or embedded in said base layer in the thickness direction thereof,
    wherein the blackhead-removing face pack sheet is to be attached to a skin under the condition that the pack material layer is in contact with moisture so that adhesion to the skin is obtained when the moisture has been evaporated thereby exhibiting a blackhead-removing function.

2. The blackhead-removing face pack sheet according to claim 1 wherein said copolymer has been copolymerized at a ratio of vinyl acetate to N-vinyl-2-pyrrolidone of 5:95 to 95:5.

3. The blackhead-removing face pack sheet according to claim 1 wherein said pack material layer has a content of said copolymer of 20–90% by weight.

4. The blackhead-removing face pack sheet according to claim 1 wherein said pack material contains at least one of vinyl acetate homopolymer and N-vinyl-2-pyrrolidone homopolymer.

5. The blackhead-removing face pack sheet according to claim 1 wherein said base layer comprises a porous material.

6. The blackhead-removing face pack sheet according to claim 5 wherein said base layer has a surface on which said pack material layer is disposed, and said surface of said base material layer has been subjected to a hydrophilization treatment.

7. The blackhead-removing face pack sheet according to claim 1 wherein said pack material layer is formed by coating or transfer.

8. The blackhead-removing face pack sheet according to claim 1 wherein said pack material layer contains a plasticizer which has a plasticizing action on said copolymer.

9. The blackhead-removing face pack sheet according to claim 1 wherein said pack material layer contains a filler.

10. The blackhead-removing face pack sheet according to claim 1 wherein said pack material layer contains a medium comprising at least one of a lower alcohol and water.

11. A method for making a blackhead-removing face pack sheet, comprising the steps of:
    providing gas-permeable and flexible base layer; and
    coating a pack material that is soluble in water and contains a copolymer of vinyl acetate and N-vinyl-2-pyrrolidone having an average molecular weight of 10,000–500,000 as its primary ingredient on one side of the base layer so that the substance constituting said pack material layer is partly impregnated or embedded in said base layer in the thickness direction thereof, and then drying the pack material to form a pack material layer,
    wherein the blackhead-removing face pack sheet is to be attached to a skin under the condition that the pack material layer is in contact with moisture so that adhesion to the skin is obtained when the moisture has been evaporated thereby exhibiting a blackhead-removing function.

12. The method for making a blackhead-removing face pack sheet according to claim 11 wherein said pack material layer contains at least one of vinyl acetate homopolymer and N-vinyl-2-pyrrolidone homopolymer.

13. A method for making a blackhead-removing face pack sheet, comprising the steps of:
    providing a gas-permeable and flexible base layer; and
    joining a pack material layer formed of a pack material that is soluble in water and contains a copolymer of vinyl acetate and N-vinyl-2-pyrrolidone having an average molecular weight of 10,000–500,000 as its primary ingredient onto one side of the base layer so that the substance constituting said pack material layer is partly impregnated or embedded in said base layer in the thickness direction thereof, by transferring the pack material onto the base layer, thereby forming a blackhead-removing face pack sheet which is to be attached to a skin under the condition that the pack material layer is in contact with moisture, so that adhesion to the skin is obtained when the moisture has been evaporated, thereby exhibiting a blackhead-removing function.

14. The method for making a blackhead-removing face pack sheet according to claim 13 wherein said pack material layer contains at least one of vinyl acetate homopolymer and N-vinyl-2-pyrrolidone homopolymer.

15. A method for making a blackhead-removing face pack sheet including a laminate which comprises a gas-permeable and flexible base layer and a pack material layer formed of a pack material that is soluble in water and contains a copolymer of vinyl acetate and N-vinyl-2-pyrrolidone having an average molecular weight of 10,000–500,000 as its primary ingredient, wherein the blackhead-removing face pack sheet is to be attached to a skin under the condition that the pack material layer is in contact with moisture, so that adhesion to the skin is obtained when the moisture has been evaporated, thereby exhibiting a blackhead-removing function, the method comprising the steps of:
    forming the pack material layer on a transfer medium;
    moistening said pack material layer and/or said base layer with water; and transferring the pack material layer from the transfer medium onto one surface of said base layer to join the pack material layer and the base layer, and pressing both the pack material layer and the base layer together so that the substance constituting said pack material layer is partly impregnated or embedded in said base layer in the thickness direction thereof.

16. A blackhead-removing face pack sheet including a laminate, which comprises:

a gas-permeable and flexible base layer; and a pack material layer formed of a pack material that is soluble in water and contains a copolymer of vinyl acetate and N-vinyl-2-pyrrolidone having an average molecular weight of 10,000–500,000 as its primary ingredient, said pack material layer containing a plasticizer which has a plasticizing action on said copolymer, a filler and a medium comprising at least one of lower alcohol and water, and said pack material layer being laminated onto the base layer so that the substance constituting said pack material layer is partly impregnated or embedded in said base layer in the thickness direction thereof, wherein the blackhead-removing face pack sheet is to be attached to a skin under the condition that the pack material layer is in contact with moisture so that adhesion to the skin is obtained when the moisture has been evaporated thereby exhibits a blackhead-removing function.

17. The blackhead-removing face pack sheet according to claim 1 wherein the pack material layer is embedded in the base layer in range from about 1% to about 80% of the thickness of the base layer.

18. The blackhead-removing face pack sheet according to claim 1 wherein the pack material layer is embedded in the base layer in range from about 5% to about 50% of the thickness of the base layer.

* * * * *